United States Patent [19]

Lumma, Jr. et al.

[11] 4,078,063
[45] Mar. 7, 1978

[54] PIPERAZINYLPYRIDINES

[75] Inventors: William C. Lumma, Jr., Pennsburg; Walfred S. Saari, Lansdale, both of Pa.

[73] Assignee: Merck & Co., Inc., Rahway, N.J.

[21] Appl. No.: 726,713

[22] Filed: Sep. 24, 1976

[51] Int. Cl.$^2$ .................. C07D 401/04; A61K 31/495
[52] U.S. Cl. .................................. 424/250; 260/268 H
[58] Field of Search .................... 260/268 H; 424/250

[56] References Cited

U.S. PATENT DOCUMENTS

| 3,699,107 | 10/1972 | Schindler et al. | 260/268 H |
| 3,773,951 | 11/1973 | Rodriguez | 424/250 |
| 3,828,046 | 8/1974 | Doerhoefer | 260/268 TR |
| 3,862,157 | 1/1975 | Wiskott | 260/268 H |
| 3,980,652 | 9/1976 | Delarge et al. | 260/268 H |
| 3,991,057 | 11/1976 | Delarge et al. | 260/268 H |

Primary Examiner—Donald G. Daus
Assistant Examiner—Jose Tovar
Attorney, Agent, or Firm—Rudolph J. Anderson, Jr.; Harry E. Westlake, Jr.; William H. Nicholson

[57] ABSTRACT

Compounds of the formula:

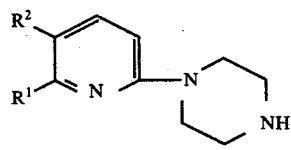

and their N-oxides and acid-addition salts are disclosed having pharmacological activity as anorexic agents.

5 Claims, No Drawings

PIPERAZINYLPYRIDINES

BACKGROUND OF THE INVENTION

This invention relates to novel piperazinylpyridines having anorexic activity, to a method of preparing these novel compounds, to pharmaceutical formulations containing the anorexic compounds, and to methods of administering the anorexic agents to an animal or human.

Obesity is a fairly common condition and a potentially serious one in view of the correlation between incidence of various diseases and the degree to which a person is overweight. For example, obese persons succumb statistically more frequently to cardiovascular renal disease than do persons of normal weight. Obesity likewise results in higher death rates from diabetes, nephritis, pneumonia, cirrhosis, appendicitis and postoperative complications. Since obesity often occurs simply as a consequence of excessive intake of calories, good management of the condition in these cases can be achieved by restricting the caloric intake. Frequently, however, the patient has difficulty in initiating and maintaining dietary restrictions, making it necessary to employ anorexigenic drugs as adjuvants to therapy.

Accordingly, it is an object of the present invention to provide novel piperazinylpyridines which are effective anorexic agents. Another object is to provide pharmaceutical formulations for administration of these anorexic agents. Further objects are to provide methods for preparing the piperazinylpyridines and for administering the anorexic agents of the present invention to a mammalian animal or human.

DETAILED DESCRIPTION

The novel compounds of the present invention are of structural formula:

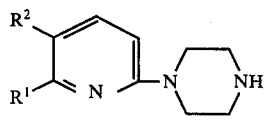

or pharmaceutically acceptable salt thereof, wherein $R^1$ is
  (1) halo, especially chloro,
  (2) trifluoromethyl,
  (3) hydrogen,
  (4) di(lower alkyl)amino, especially of 2-6 carbon atoms,
  (5) phenylthio, or
  (6) lower alkylthio, especially $C_{1-3}$ alkylthio, and
$R^2$ is
  (1) halo, especially chloro,
  (2) phenyl, or
  (3) hydrogen,
with the proviso that $R^1$ and $R^2$ are not both hydrogen.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic, methanesulfonic, or ethane disulfonic.

The novel compounds of the present invention are prepared by reaction of a 2-X-pyridine of formula I with piperazine of formula II.

The reaction sequence is as follows:

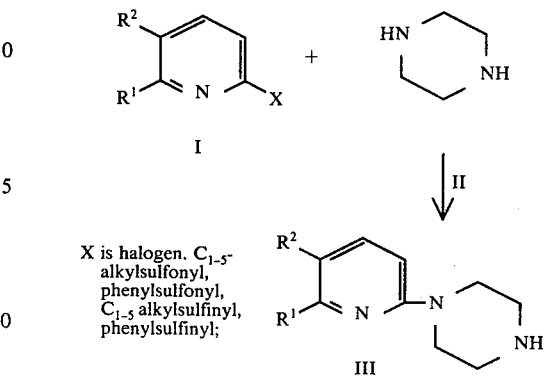

X is halogen, $C_{1-5}$-alkylsulfonyl, phenylsulfonyl, $C_{1-5}$ alkylsulfinyl, phenylsulfinyl;

The reaction takes place at temperatures ranging from about ambient to about 200° C., preferably under an inert atmosphere, e.g. $N_2$, He or Ar, until a substantial amount of desired compound of formula III is obtained, typically for a period of from about 0.5 to about 8 hours, preferably from about 1 to about 6 hours.

In the novel method of treatment of the present invention, a compound of structural formula:

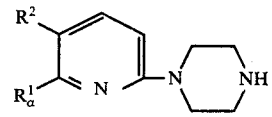

or pharmaceutically acceptable salt thereof, wherein $R_a^1$
  (1) halo, especially chloro,
  (2) lower alkoxy, especially $C_{1-4}$ alkoxy, such as methoxy,
  (3) trifluoromethyl,
  (4) hydrogen
  (5) di(lower alkyl)amino, especially of 2-6 carbon atoms,
  (6) phenylthio,
  (7) lower alkylthio, especially $C_{1-3}$ alkylthio, or
  (8) lower alkyl, especially $C_{1-3}$ alkyl, such as methyl; and
$R^2$ is
  (1) halo, especially chloro,
  (2) phenyl, or
  (3) hydrogen,
is administered as anorexic agents in amounts ranging from about 0.01 to about 20 mg. per kg. of body weight per day, preferably from about 0.1 to about 10 mg. per kg. of body weight per day in a single dose or in 2 to 4 divided doses.

The compounds active in the novel method of treatment of the present invention in the described dosages may be administered orally, intraperitoneally, subcutaneously, intramuscularly, or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

In addition to the anorexic activity described above, the compounds active in the novel method of treatment of this invention pharmacologically infuence serotonin levels in a manner that suggests they are also useful as antidepressant, antihypertensive, analgesic and sleep inducings agents. For these purposes, the same routes of administration, and pharmaceutical formulations as described above would be employed.

The following examples illustrate the present invention without, however, limiting the same thereto. Unless otherwise indicated, all temperatures are expressed in degress Celsius.

EXAMPLE 1

5-Phenyl-2-(1-piperazinyl)pyridine Hydrogen Fumarate

A mixture of 2-chloro-5-phenylpyridine (2.0 g.) and piperazine (2.5 g.) is heated 5 hours at 140° with stirring under nitrogen, cooled, and partitioned between ice cold aqueous sodium hydroxide and benzene. The combined benzene extracts are washed with dilute aqueous sodium hydroxide, dried over sodium sulfate, filtered, and concentrated in vacuo to an oil which is dissolved in 15 ml. of isopropanol. Upon adding 50 ml. of 0.4 molar solution of fumaric acid in 95% aqueous ethanol, the title compound crystallizes as a white solid, m.p. 220-221° (dec.).

EXAMPLE 2

6-Chloro-2-(1-piperazinyl)pyridine Hydrochloride 2,6-Dichloropyridine (14.8 g., 0.100 mole) and piperazine (15 g.) are combined in 150 ml. acetonitrile and the mixture refluxed on the steam bath for 4 hr. The mixture is concentrated in vacuo and the residue partitioned between benzene and water. The benzene extracts are stirred with 125 ml. of 1N aqueous hydrochloric acid and the two-phase mixture filtered to collect the title compound which is recrystallized from methanol, m.p. 284°-286° C.

Following the procedure substantially as described in either of Example 1 or Example 2, but substituting for the 2-chloro-5-phenylpyridine and 2,6-dichloropyridine, respectively, used therein, an equimolecular amount of the 2-chloropyridines described in Table I, there are produced the 2-(1-piperazinyl)pyridines also described in Table I by the following chemical process:

Table I

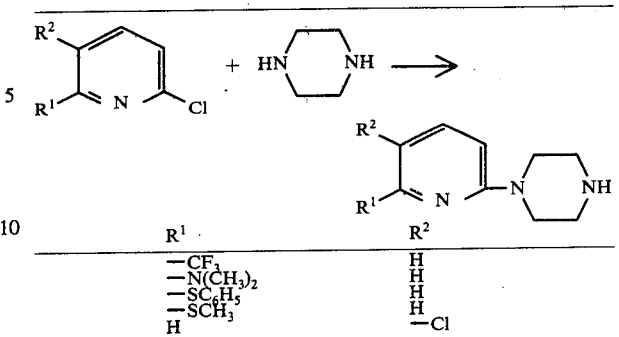

| $R^1$ | $R^2$ |
|---|---|
| $-CF_3$ | H |
| $-N(CH_3)_2$ | H |
| $-SC_6H_5$ | H |
| $-SCH_3$ | H |
| H | $-Cl$ |

EXAMPLE 3

| Preparation of Capsule Formulation | |
|---|---|
| Ingredient | Milligrams per Capsule |
| 6-chloro-2-(1-piperazinyl)-pyridine hydrochloride | 6 |
| Starch | 87 |
| Magnesium stearate | 7 |

The active ingredient, starch and magnesium stearate are blended together. The mixture is used to fill hard shell capsules of a suitable size at a fill weight of 100 milligrams per capsule.

What is claimed is:

1. The compound 6-chloro-2-(1-piperazinyl)pyridine or a pharmaceutically acceptable salt thereof.

2. A method of decreasing food intake which comprises administering to a patient in need of such treatment an effective amount of a compound of formula

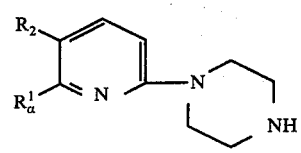

or pharmaceutically acceptable salt thereof, wherein
$R_a^1$ is hydrogen, halo, trifluoromethyl, lower alkoxy, phenylthio, lower alkylthio, di(lower alkyl)amino, or lower alkyl; and
$R^2$ is hydrogen, halo or phenyl.

3. A method of decreasing food intake which comprises administering to a patient in need of such treatment an effective amount of 6-chloro-2-(1-piperazinyl)pyridine or a pharmaceutically acceptable salt thereof.

4. A pharmaceutical anorectic compostion comprising a pharmaceutical carrier and an effective amount of 6-chloro-2-(1-piperazinyl)pyridine or a pharmaceutically acceptable salt thereof.

5. A method of decreasing food intake which comprises administering to a patient in need of such treatment an effective amount of a compound of formula:

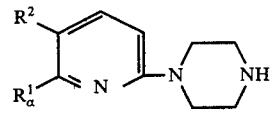

or a pharmaceutically acceptable salt thereof, wherein:
$R_a^1$ is chloro, $C_{1-4}$alkoxy, trifluoromethyl, hydrogen, $C_{2-6}$-di(loweralkyl)amino, phenylthio, $C_{1-3}$alkylthio or $C_{1-3}$ alkyl; and
$R^2$ is chloro, phenyl or hydrogen.

* * * * *